United States Patent
Baumeister et al.

(10) Patent No.: US 6,702,996 B1
(45) Date of Patent: Mar. 9, 2004

(54) METHOD FOR INVESTIGATING THE SUITABILITY OF A MATERIAL AS A MEDICAMENT

(75) Inventors: Ralf Baumeister, Freiburg (DE); Nicole Wittenburg, Planegg (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/980,007

(22) PCT Filed: May 30, 2000

(86) PCT No.: PCT/EP00/04950

§ 371 (c)(1),
(2), (4) Date: Nov. 30, 2001

(87) PCT Pub. No.: WO00/73491

PCT Pub. Date: Dec. 7, 2000

(30) Foreign Application Priority Data

May 31, 1999 (DE) .......................................... 199 24 929

(51) Int. Cl.⁷ ................................................. A61K 51/00
(52) U.S. Cl. ...................................................... 424/9.2
(58) Field of Search .............................. 424/9.2; 435/4; 800/9

(56) References Cited

U.S. PATENT DOCUMENTS 6,444,665 B1 * 9/2002 Helton et al. ............... 514/220

FOREIGN PATENT DOCUMENTS

| DE | 30 18 900 | 11/1980 |
| DE | 41 06 279 | 9/1992 |
| DE | 41 40 440 | 6/1993 |
| WO | 90/09096 | 8/1990 |
| WO | 00/34438 | 6/2000 |

OTHER PUBLICATIONS

N. Wittenburg, et al., "Thermal Avoidance Behaviour: It is pain—but no in the a . . . ", Worm Breeder's Gazette 15(2); Feb. 24, 1998, pp. 1–2.
N. Wittenburg, et al., "C. elegans as a new animal model to study the genetics of nociception", European Worm Meeting, Abstract t37, (1998), p. 1.
N. Wittenburg, et al., "Thermal Avoidance: a novel approach to study nociception in C. elegans", International Worm Meeting Abstract 914, (1999).
N. Wittenburg, et al., "Thermal avoidance in Caenorhabditis elegans: An approach to the study of nicieption", Proc. Natl. Acad. Sci. USA, vol. 96, Aug., 1999, pp. 10477–10482.
Tominaga, et al., "The Cloned Capsaicin Receptor Integrates Multiple Pain–producing Stimuli", Neuron, 21, Sep. 1998, p. 531–543.
Kaplan, et al., "A dual mechanosensory and chemosensory neuron in caenorhabditis elegans," Proc. Natl. Acad. Sci. USA, vol. 90, Mar. 1993, pp. 2227–2231.
Samoiloff, et al., "Regulation of Nematode Behavior by Physical Means", Experimental Parasitology, 33(2), 1973, pp. 253–262.
Ahringer, J., "Turn to the Worm", Current Opinion in Genetics & Development, 7(3), 1997, pp. 410–415.

* cited by examiner

*Primary Examiner*—Michael G. Hartley
(74) *Attorney, Agent, or Firm*—Heller Ehram White and McAuliffe

(57) ABSTRACT

A method of investigating the suitability of a material as a medicament is disclosed. The method according to the invention uses a nematode which has been brought into contact with the test substance and which is then exposed to a local thermal stimulus.

9 Claims, 1 Drawing Sheet

METHOD FOR INVESTIGATING THE SUITABILITY OF A MATERIAL AS A MEDICAMENT

This application is a 371 of PCT/EP00/04950, filed May 30, 2000.

The present invention relates to a method of investigating the suitability of a material as a medicament for mammals, particularly humans. The invention further relates to a kit with which such a method can be put into practice.

The development of new medicaments takes a total of 10 to 12 years on average. A large part of this time is taken up initially in targeting a material which may be suitable for a specific indication. The number of initially screened substances frequently runs into hundreds of thousands. There is therefore a particular need for a simple and rapid test method by which the substances to be examined can basically be categorized as suitable or unsuitable, but no methods are currently known which are capable of predicting a possible efficacy in humans (or other mammals) with a high degree of reliability. Animal models are of course available for this purpose, but they are either unreliable and/or very expensive in terms of their predictive value. Moreover, conventional animal models are increasingly being generally rejected because they cause the animals (for example dogs and monkeys) to suffer. On the other hand, animal models are normally required to have a great similarity to the human organism so as to guarantee some likelihood that the knowledge gained from the animal experiments will be applicable to humans.

There is a particular need for an animal model which has a high predictive value and which can either replace conventional animal models or at least reduce the scale of experiments on higher organisms (such as mammals). This need is particularly relevant in the search for drugs which influence the human perception of pain, e.g. analgesics and sedatives.

The present invention goes back to the discovery that nematodes (threadworms) exhibit a retraction reflex to a local thermal stimulus and that this reflex can be influenced by active substances that affect the human perception of pain. The present invention is based on the knowledge that certain threadworms react in a defined way to locally applied thermal stimuli and that the reflex to this stimulus allows a prediction to be made as regards the effect of a particular material on the sensation of pain in humans (including mammals).

Figure 1:
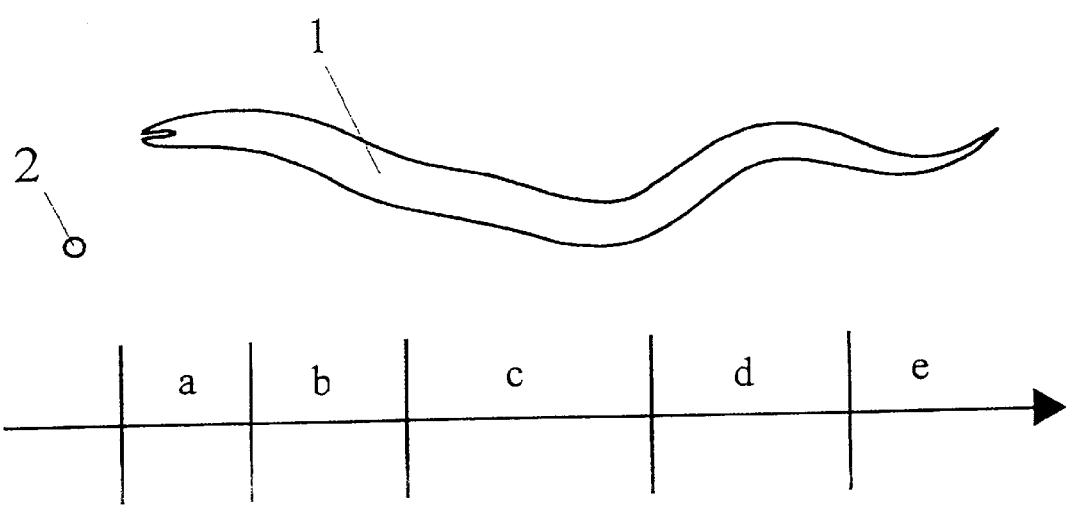
FIGURE 1 shows a diagram of a worm, with a length of about 1.3 mm and a diameter of 80 $\mu$m. The worm (1) may be irradiated with a laser beam, causing localized warming. The laser spot (2) has a diameter of about 30 $\mu$m and is preferably directed at the head or tail of the worm. The head region corresponds to regions a and b of the figure, and the tail region is located at region e of the FIGURE.

The invention consequently consists of a method of investigating the suitability of a material as a medicament using at least one nematode which has been exposed to the test material, and exposing this nematode to a local thermal stimulus, preferably outside the temperature range 13–26° C. As a result of this stimulus, the nematode exhibits a reflex which can deviate from normal reflex behaviour (normal behaviour) depending on the material used. The thermal stimulus is preferably limited to an area of 10–100 $\mu$m$^2$. This stimulus can be produced by means of a laser or a heated wire tip.

As a rule, to establish suitability or non-suitability, it will suffice qualitatively to record the deviation from previously observed normal behaviour. As the normal behaviour is very distinctive and significant (cf. details below), a deviation will be easy to observe. Normally, it will be possible to examine relatively large populations of nematodes and express a qualitative deviation substantially as a percentage, namely as a percentage of animals which no longer exhibit a particular behaviour after they have been exposed to the material and the thermal stimulus has been applied. However, a particular suitability can also manifest itself as an intensification of the reflex behaviour, especially in the case of algesics. More recently, it has also become possible to use mutants of the nematodes whose reflex behaviour towards the thermal stimulus is not so distinctive and which then exhibit an intensified reflex behaviour after the administration of an algesiogenic substance.

However, the use of the method according to the invention is not restricted to a medicament that influences pain. An effect on the sensation of pain in a typical human signifies nothing other than the fact that particular receptors are responding to a particular compound. However, receptors which cause specific effects often have certain similarities to one another; thus, for example, pain-relieving substances also have particular pharmacological effects in other ranges of indications. Such ranges of indications pertain to anti-inflammatory, antipyretic, sedative, muscle-relaxing and similar effects, inter alia. In the context of the present invention, pain is understood as meaning any type of pain, for example muscular pain or headache/migraine.

This behaviour has been studied in greater detail on nematodes of the genus Caenorhabditis and especially on *Caenorhabditis elegans* or mutants thereof. A distinctive reflex to local thermal stimuli is observed in this threadworm in the fully-grown state (but not in the diapause or so-called permanent larvae). It is clear that these thermal stimuli stimulate nociceptors which lead to a reflex-like retraction behaviour. This behaviour is triggered in a particularly striking way when exposing the head or tail region of *C. elegans* either to ice-cold temperatures or to local warming to at least 28° C. It has been established that this behaviour does not depend on the temperature at which the nematodes were raised (larval development). Rather, in response to the local action of so-called noxious heat, i.e. potentially cytotoxic heat, *C. elegans* exhibits a behaviour which can lie between a rapid reflex retraction and a slow retraction from the site of application.

It has now been established, surprisingly, that nematodes that have been exposed to particular chemical substances with a pharmacological action in humans exhibit deviations from the normal behaviour described above. The nematodes can be exposed to the test materials in a very wide variety of ways. For example, it is possible to cultivate the animals in Petri dishes with an agar containing the substances of interest. Another possibility, however, is simply to bathe the animals in the test materials. This variant is not only particularly simple but also makes it possible to standardize the concentrations more easily. A study is carried out on well-fed populations of animals which are then incubated with different solutions of the materials in different concentrations. The inventors' experiments have now shown that substances which cause pain as well as those which alleviate pain have a marked effect on the reflex behaviour of the nematode. Thus the reflex behaviour can be influenced on the one hand by a substance which causes hyperalgesia, such as capsaicin, and on the other hand by an effective and specific capsaicin inhibitor, i.e. capzazepine. This observation, namely the modification of reflex behaviour with agonist/antagonist pairs recognized by mammals, makes it possible to draw conclusions about the possible efficacy of a material which is to be examined for its suitability as a medicament.

The FIGURE diagrammatically shows a worm (1) with a length of about 1.3 mm and a diameter of 80 $\mu$m. The worm (1) can be irradiated with a focused laser beam, causing local warming. The laser spot (2) has a diameter of about 30 $\mu$m and is preferably directed at the head or tail regions of the worm in the method according to the invention. The head region approximately corresponds to regions a and b in the illustration and the tail region is region e. In wild-type *C. elegans*, the reflex behaviour discussed here is normally observed in the different regions with the following frequency: a—98%, b—71%, c—0%, d—0%, e—49%.

The inventors' experiments have thus shown that the use of *C. elegans* as an animal model for studying materials in terms of their suitability as medicaments in humans or other mammals allows reliable predictions to be made, especially where the sensation or perception of pain is involved, both in terms of algesic or hyperalgesic effects and in terms of analgesic effects. It has been found that the so-called nociceptors of *C. elegans* can be caused to respond simply by means of a heated wire tip (e.g. microsolder gun, heated spatula etc.) or a focused laser beam. A normal reflex to a thermal stimulus of e.g. 32–40° C. in the head region of the nematode can be described as follows:

I) Rapid reflexive retraction by at least one whole body length and subsequent orientation of the head in another direction.

II) Rapid reflexive retraction, but without backward motion.

III) Slow retraction.

It was observed that normally at least 80% of the animals exhibited a behaviour as in I).

To standardize the method according to the invention, it is advisable to use a laser because this enables a constant thermal stimulus to be applied to the nematodes in a reproducible manner. As the laser beam also causes no permanent damage to the nematodes, the method according to the invention can be carried out repeatedly.

The invention is illustrated in the following Examples.

EXAMPLES

The well-fed test animals (*C. elegans*) (about 100; length about 1.3 mm; diameter 80 $\mu$m) were irradiated in the experiments with an infrared laser (685±0.5 nm). The laser beam was always focused on a spot of diameter 30 $\mu$m in the head region of the animal, a local warming to 33.5±1° C. being observed on an agar surface. To examine the animals' behaviour in greater detail, they were exposed to a nociceptive stimulus, after which they were incubated in capsaicin at concentrations varying from 1 to 100 $\mu$M. A strong reaction was still being observed 1 h after incubation. The evidence for this reaction is that over 90% of the animals exhibited a reflex as in I), whereas only 80% of the animals showed this reflex in the control group. This reaction could be observed even more clearly in mutants whose normal behaviour is such that only 70% of the animals react as in I).

These Examples show that the reflex of interest here can be intensified by substances which have a hyperalgesic effect in humans. A reverse (i.e. attenuated) reflex behaviour is observed for substances capable of relieving pain.

What is claimed is:

1. Method of investigating the suitability of a material as a medicament concerned with the sensation of pain, wherein 1. at least one nematode is used which has been exposed to the material,
   2. the nematode is exposed to a local thermal stimulus, and
   3. a reaction is recorded if it deviates from normal behaviour.

2. Method according to claim 1, wherein the nematode belongs to the strain Nematode.

3. Method according to claim 2, wherein the nematode belongs to the genus Caenorhabditis.

4. Method according to claim 1, wherein the sensation of pain is reduced or relieved.

5. Method according to claim 1, wherein the nematode is exposed to the thermal stimulus in its head or tail region.

6. Method according to claim 5, wherein the thermal stimulus is outside the temperature range 13–26° C.

7. Method according to claim 6, wherein the thermal stimulus produces a temperature of at least 28° C. at the site at which the nematode is exposed to the thermal stimulus.

8. Method according to claim 1, wherein the thermal stimulus is limited to a local area of 10–100 $\mu m^2$.

9. Method according to claim 1, wherein the stimulus is produced by means of a laser or a heated wire tip.

* * * * *